United States Patent [19]
Lee

[11] Patent Number: 5,847,261
[45] Date of Patent: Dec. 8, 1998

[54] POLARITY DISCRIMINATING METHOD AND SIGNAL PROCESSING CIRCUIT FOR A VAPOR SENSOR IN A MICROWAVE OVEN

[75] Inventor: Charng-Gwon Lee, Incheon, Rep. of Korea

[73] Assignee: Daewoo Electronics Co., Ltd., Seoul, Rep. of Korea

[21] Appl. No.: 614,547

[22] Filed: Mar. 13, 1996

[30] Foreign Application Priority Data

Sep. 29, 1995 [KR] Rep. of Korea ................. 1995-33038

[51] Int. Cl.[6] ........................... G01N 25/26; G01M 19/00
[52] U.S. Cl. ............................... 73/1.07; 219/707
[58] Field of Search ................. 73/1 G, 25.04, 73/1.07, 1.06; 219/707

[56] References Cited

U.S. PATENT DOCUMENTS

| | | | |
|---|---|---|---|
| 4,336,433 | 6/1982 | Yokozeki | 73/335.05 X |
| 5,235,148 | 8/1993 | Yamaguchi et al. | 219/707 |
| 5,395,633 | 3/1995 | Lee | 426/233 |
| 5,436,433 | 7/1995 | Kim et al. | 219/703 |
| 5,445,009 | 8/1995 | Yang et al. | 73/29.01 |
| 5,744,785 | 4/1998 | Lee | 219/707 |

*Primary Examiner*—Thomas P. Noland
*Attorney, Agent, or Firm*—Pillsbury Madison & Sutro LLP

[57] ABSTRACT

A polarity discriminating method and signal processing circuit for a vapor sensor in a microwave oven is disclosed. The control section operates a fan motor so as to discriminate the polarity of a detecting signal supplied from the vapor sensor, which is varied with the wind produced by the fan motor. After the control section initializes variables of counters, the control section compares the magnitude of the signal-processed detecting signal supplied from the detecting signal processing circuit section with the magnitude of a reference detecting signal in a specified range on the phase coordinate axis. Meanwhile, the control section discriminates whether the slope of the curve of the signal-processed detecting signal is positive or negative, thereby discriminating whether the vapor sensor operates in a positive polarity mode or negative polarity mode. Furthermore, the configuration of the signal processing circuit for the vapor sensor in the microwave oven is simplified, so that the unit cost required for manufacturing the circuit decreases and the volume of the circuit is reduced. Therefore, the malfunction of the electronic circuit section installed in the microwave oven is prevented.

5 Claims, 4 Drawing Sheets

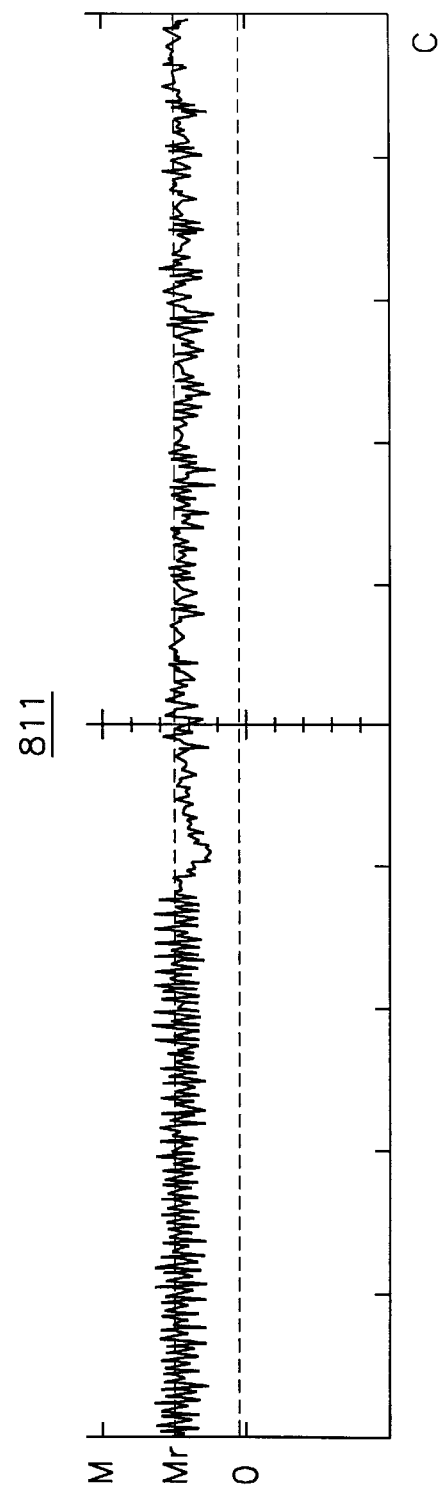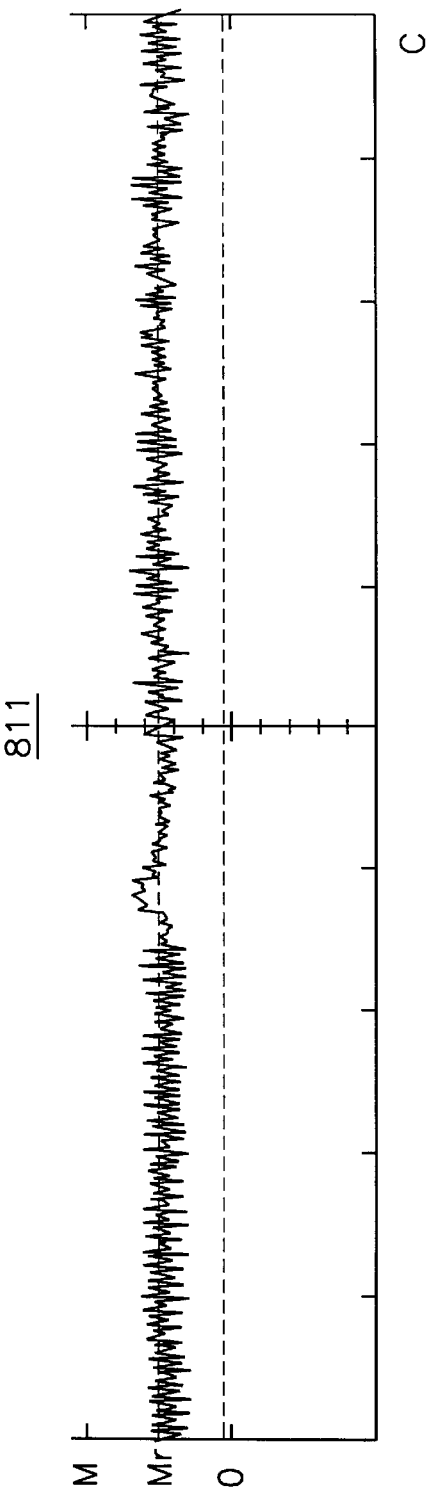

POLARITY DISCRIMINATING METHOD AND SIGNAL PROCESSING CIRCUIT FOR A VAPOR SENSOR IN A MICROWAVE OVEN

BACKGROUND OF THE INVENTION

1. Field of the Invention

The present invention relates to a polarity discriminating method and a signal processing circuit for a vapor sensor in a microwave oven. More particularly, the present invention relates to the polarity discriminating method and the signal processing circuit in which a varying polarity of a vapor sensor is automatically discriminated in a microwave oven equipped with the vapor sensor therein and a malfunction of an electric circuit in the microwave oven is prevented while an automatic cooking operation is being performed.

2. Description of the Prior Art

FIG. 1 is a schematic construction view for showing an internal structure of a general microwave oven equipped with a vapor sensor therein. As shown in FIG. 1, in a microwave oven 10 for controlling an automatic cooking operation by using the vapor sensor, while a high voltage transformer 100 applies high voltage electricity to a magnetron 200, microwave is generated from magnetron 200, and the microwave heats food within a cooking chamber formed by a cavity 300.

Meanwhile, water vapor is generated from the heated food, then discharged along the air flow which effuses from first blow holes 311 formed in the upper portion of a first sidewall 310 of cavity 300 by a blowing operation of a fan motor 400 and passes sequentially through first exhaust holes 321 formed in the lower portion of a second sidewall 320 disposed in opposition to first sidewall 310 and first discharge holes 500. Also, the water vapor is discharged along the air flow which sequentially passes through second exhaust holes 331 formed in a central portion of a ceiling portion 330 of cavity 300, through a wind path 500, and through second discharge holes 700. Then, the energy of the water vapor discharged along wind path 500 is sensed by a vapor sensor 800 which also has the characteristics of a piezo-electric device attached to inlets of second discharge holes 700, so that the heating time is adjusted to an optimum time during the automatic cooking operation.

FIG. 2 is a construction view for showing the internal structure of the vapor sensor. As shown in FIG. 2, vapor sensor 800, called superconducting sensor, has the shape of a disc, and has a structure in which a first disc 820 made of ceramic is located in the central portion of the disc and a second disc 830 surrounds first disc 820. A first electrode terminal 821 and a second electrode terminal 831 are respectively fixed to be connected with first disc 820 and second disc 830. When vapor sensor 800 sucks in or discharges heat, vapor sensor 800 generates a detecting signal 810 through first electrode terminal 821 and second electrode terminal 831. At this time, polarity of vapor sensor 800, i.e., polarity of first and second electrode terminal electrode terminals 821 and 831, is specified by agreement among the users. Detecting signal 810 has the waveform of an alternating current signal and the magnitude of detecting signal 810 is proportional to the amount of heat variation rather than to the absolute heat value. For example, when there is no variation of the heat, both the first detecting signal at 0° C. and the second detecting signal at 100° C. have very small positive values which are similar to each other. For another example, if the ambient temperature increases from 0° C. to 10° C., the value of detecting signal 810 increases in the positive direction. On the contrary, if the ambient temperature decreases from 100° C. to 90° C., the value of detecting signal 810 decreases from the positive direction to the negative direction. The reducing amount of detecting signal 810 is proportional to the discharging degree of the heat. That is to say, if the ambient temperature continues to decrease from 100° C., the polarity of detecting signal 810 outputted from first and second electrode terminals 821 and 831 of vapor sensor 800, is reversed from the positive direction to the negative direction.

One example of an automatic thawing device of microwave oven and control method thereof is disclosed in U.S. Pat. No. 5,436,433 (issued to Kim et al.). Here, a turntable is rotatably placed in a cooking chamber. A gas sensor is placed about an exhaust port of the microwave oven and senses the amount of gas or vapor exhausted from the cooking chamber through the exhaust port during a thawing operation, and outputs a gas amount signal to a microprocessor. The microprocessor calculates the thawing time by an operation activated by an output signal of the gas sensor and outputs a thawing control signal for driving the microwave oven. An output drive means controls the output level of electromagnetic wave of high frequency in accordance with the thawing control signal of the microprocessor. The magnetron generates the electromagnetic wave of high frequency in accordance with the output signal of the drive means for the thawing time. A power source supplies electric power to the thawing device in accordance with the thawing control signal of the microprocessor.

U.S. Pat. No. 5,445,009 (issued to Yang et al.) is an example of an apparatus and a method for detecting humidity in a microwave oven. The apparatus and method for removing the influence of microwave noise without any shielding parts increases the reliability of detected humidity information. According to this patent, the cumulative difference of humidity values sensed by a humidity sensor is calculated for each half period of a commercial alternating current frequency, oscillating and non-oscillating terms of a magnetron are determined by comparing the calculated cumulative differences with each other, and the humidity-sensed values obtained during the determined non-oscillating terms of the magnetron are used as humidity information for automatic cooking control. In order to even further remove the influence of microwave noise, the humidity sensor may include capacitors for bypassing the microwave noise introduced into the sensor.

As one example of a method for automatically controlling the cooking of food with a low moisture content, U.S. Pat. No. 5,395,633 (issued to Lee et al.) discloses an automatic cooking control method capable of cooking food with a low moisture content at an optimum by utilizing a variation in an output voltage of a humidity sensor. When a key signal corresponding to the food with the low moisture content is received, an initialization is performed. Then, the maximum voltage indicative of the maximum humidity is determined by reading the continuously increasing output voltage from the humidity sensor 10 times for 10 seconds. After the determination of the maximum voltage, a determination is made whether the output voltage has reached a sensing voltage corresponding to a voltage obtained by deducing from the maximum voltage a minute voltage varied depending on the kind of food. The cooking operation is completed when the output voltage from the humidity sensor has reached the sensing voltage.

As described above, in the case of a conventional microwave oven which controls the automatic cooking operation by using the vapor sensor, in general, detecting signal 810 generated from vapor sensor 800 oscillates up and down on the basis of the reference detecting signal which corresponds to an objective value. Hereinafter, "positive polarity mode" is defined as the case where detecting signal 810 is smaller than the reference detecting signal. On the contrary, "negative polarity mode" is defined as the case where detecting signal 810 is greater than the reference detecting signal. Therefore, the sign of the curve slope of detecting signal 810 has a positive or negative polarity in a specified range on the phase coordinate axis. Here, the slope means a differential value at a certain point indicated by a corresponding phase coordinate value and magnitude coordinate value. Hence, when the vapor sensor 800 sucks in or discharges the heat included water vapor which is generated from food ,placed in a cavity 300, subjected to heat and flows outward through a wind path 600, if factors of detecting signal 810 supplied from vapor sensor 800 are respectively referred to as a first detecting signal and a second detecting signal, the first detecting signal has a positive slope and the second detecting signal has a negative slope, so that these two detecting signals are apparently distinguished from each other.

When the polarity of detecting signal 810 supplied from vapor sensor 800 is reversed from the positive polarity mode to the negative polarity mode or vice versa, cooking data which differs from the cooking data obtained from experiments, is presented. Accordingly, an electronic circuit section (not shown) malfunctions by miscreconizing the cooking data during the automatic cooking operation. If the electronic circuit section frequently malfunctions, the performance and the life span of the microwave oven are reduced, so that the user misunderstands the performance of the microwave oven. As a result, both the user's expectation of reliability concerning the performance of microwave oven and the consumer's intention with which the microwave oven is purchased, are severely reduced.

SUMMARY OF THE INVENTION

Accordingly, it is a first object of the present invention to provide a method for automatically discriminating whether a detecting signal supplied from a vapor sensor varied by the wind generated by means of a fan motor has a positive polarity mode or negative polarity mode in a microwave oven equipped with a vapor sensor therein.

It is a second object of the present invention to provide a detecting signal processing circuit (hereinafter, referred to as "detecting signal processing circuit section") for outputting only a positive value by signal-processing, executed by an amplifying device, the detecting signal which has the waveform of an alternating current signal and is supplied from the vapor sensor.

In order to achieve the above first object of the present invention, the present invention provides a polarity discriminating method for a vapor sensor in a microwave oven, which comprises the steps of:

(i) operating a blowing means for an operating time by a control means so as to remove water vapor which remains in a cavity, thereby air-cooling the cavity while food is being cooked by using a microwave oven equipped with a vapor sensor therein;

(ii) initializing to zero both a first variable of a first counter and a second variable of a second counter in order to measure a magnitude of a signal-processed detecting signal supplied from a detecting signal processing circuit section which inputs and signal-processes a detecting signal supplied from the vapor sensor;

(iii) recording the measured magnitude of the signal-processed detecting signal supplied from the detecting signal processing circuit section in response to the wind which is produced by the operation of the blowing means and which passes sequentially through second exhaust holes formed in a central portion of a ceiling portion of the cavity, through a wind path and through second discharge holes;

(iv) initializing to zero either the first variable of the first counter or the second variable of the second counter, and increasing either the first variable of the first counter or the second variable of the second counter by a first predetermined amount in accordance with the measured magnitude of the signal-processed detecting signal; and (v) either indicating an error state or operating a microwave generating means in accordance with either a value of the first variable of the first counter or a value of the second variable of the second counter.

Preferably, the step (i) comprises the substeps of:

(a) initializing to zero the operating time of the blowing means;

(b) increasing the operating time of the blowing means by a second predetermined amount;

(c) judging whether or not the operating time of the blowing means increased by the second predetermined amount in step (b) is greater than or equal to a predetermined time;

(d) returning to step (b) and repeating the succeeding steps when it is judged in step (c) that the operating time of the blowing means is smaller than the predetermined time; and (e) performing step (ii) when it is judged in step (c) that the operating time of the blowing means is greater than or equal to the predetermined time.

Furthermore, preferably, the step (iv) comprises the substeps of:

(f) judging whether or not the measured magnitude of the signal-processed detecting signal is smaller than or equal to a magnitude of a reference detecting signal;

(g) initializing to zero the first variable of the first counter and increasing the second variable of the second counter by the first predetermined amount when it is judged in step (f) that the magnitude of the signal-processed detecting signal is greater than the magnitude of the reference detecting signal; and (h) increasing the first variable of the first counter by the first predetermined amount and initializing to zero the second variable of the second counter when it is judged in step (f) that the magnitude of the signal-processed detecting signal is smaller than or equal to the magnitude of the reference detecting signal.

Furthermore, preferably, the step (v) comprises the substeps of:

(k) judging whether or not the second variable of the second counter increased by the first predetermined amount in step (iv), is greater than or equal to the second variable of the reference detecting signal;

(l) returning to step (iii) and repeating the succeeding steps when it is judged in step (k) that the second variable of the second counter is smaller than the second variable of the reference detecting signal;

(m) indicating an error state when it is judged in step (k) that the second variable of the second counter is greater than or equal to the second variable of the reference detecting signal;

(n) judging whether or not the first variable of the first counter increased by the first predetermined amount in step (iv) is greater than or equal to the first variable of the reference detecting signal;

(o) returning to step (iii) and repeating the succeeding steps when it is judged in step (n) that the first variable of the first counter is smaller than the first variable of the reference detecting signal; and (p) operating a microwave generating means by a load driving means when it is judged in step (n) that the first variable of the first counter is greater than or equal to the first variable of the reference detecting signal.

In order to achieve the above second object of the present invention, the present invention provides a signal processing circuit for vapor sensor in a microwave oven, which comprises:

a vapor sensor having a first electrode terminal and a second electrode terminal each of which is defined as a positive terminal and a negative terminal, and for outputting a detecting signal which is supplied from the first and second electrode terminals and which increases in the positive direction or decreases in the negative direction by sucking in or discharging the heat;

a condenser having both sides of connecting terminals thereof respectively connected with the first electrode terminal and the second electrode terminal of the vapor sensor, and for refining the waveform of the detecting signal;

a first resistor having both sides of connecting terminals thereof respectively connected with the first electrode terminal and the second electrode terminal of the vapor sensor, and for converting a current signal of the detecting signal supplied from the vapor sensor into a voltage signal;

an operational amplifier having a non-inverting(+) input terminal connected with the first electrode terminal of the vapor sensor, having an inverting(−) input terminal for inputting an external signal, having an output terminal connected with the detecting signal input terminal of a control means which is connected in the next stage thereof, and for amplifying the detecting signal supplied from the vapor sensor to provide a signal-processed detecting signal;

a second resistor for carrying out a negative feedback operation by feedbacking a part of the amplified current signal while the operational amplifier carries out amplifying operation of the detecting signal, the second resistor connected between the inverting(−) input terminal and the output terminal of the operational amplifier;

a third resistor having both sides of connecting terminals thereof respectively connected to the inverting(−) input terminal of the operational amplifier and an earth connection, and for applying a biasing voltage to the inverting(−) input terminal; and a fourth resistor having both sides of connecting terminals thereof respectively connected to the output terminal of the operational amplifier and the earth connection, and for converting a current signal into a voltage signal, whereby the detecting signal supplied from the vapor sensor is applied to a control means, a measuring point of the detecting signal is a first commonly-connecting point with which non-inverting (+) input terminal of the operational amplifier and the first electrode terminal of the vapor sensor are directly connected, the detecting signal has the waveform of an alternating current signal at the first commonly-connecting point, and the signal-processed detecting signal supplied from the output terminal of the operational amplifier has only a positive value by means of the signal processing operation of the operational amplifier.

In the polarity discriminating method and signal processing circuit for a vapor sensor in a microwave oven according to the present invention, while food is being cooked by means of the microwave oven equipped with the vapor sensor therein, the control means operates a fan motor so as to discriminate the polarity, varied with the wind produced by means of the fan motor, of a detecting signal supplied from the vapor sensor. After the control means initializes variables of counters, the control means compares the magnitude of the signal-processed detecting signal supplied from the detecting signal processing circuit section with the magnitude of a reference detecting signal in a specified range on the phase coordinate axis. Meanwhile, the control means discriminates whether the slope of the curve of the signal-processed detecting signal is positive or negative in the specified range, thereby discriminating whether the vapor sensor operates in a positive polarity mode or a negative polarity mode. Furthermore, in the signal processing circuit for the vapor sensor in the microwave oven, the configuration of the circuit is simplified, so that the unit cost required for manufacturing the circuit decreases and the volume of the circuit is reduced. Therefore, the malfunction of the electronic circuit section installed in the microwave oven is prevented, so that the performance and the life span of the microwave oven are significantly enhanced to heighten the user's sense of reliability concerning the performance of the microwave oven and to fulfill the consumer's intention with which the microwave oven is purchased.

BRIEF DESCRIPTION OF THE DRAWINGS

The above objects and other advantages of the present invention will become more apparent by describing in detail a preferred embodiment thereof with reference to the attached drawings, in which:

FIG. 5 and FIG. 6 are respectively waveform diagrams for showing the waveforms of signal-processed detecting signals supplied from the detecting signal processing circuit section shown in FIG. 3.

DESCRIPTION OF THE PREFERRED EMBODIMENT

A description will be given below in detail to the configuration and related operation of a polarity discriminating method and signal processing circuit for a vapor sensor in a microwave oven according to an embodiment of the present invention with reference to the accompanying drawings.

Figure 1:
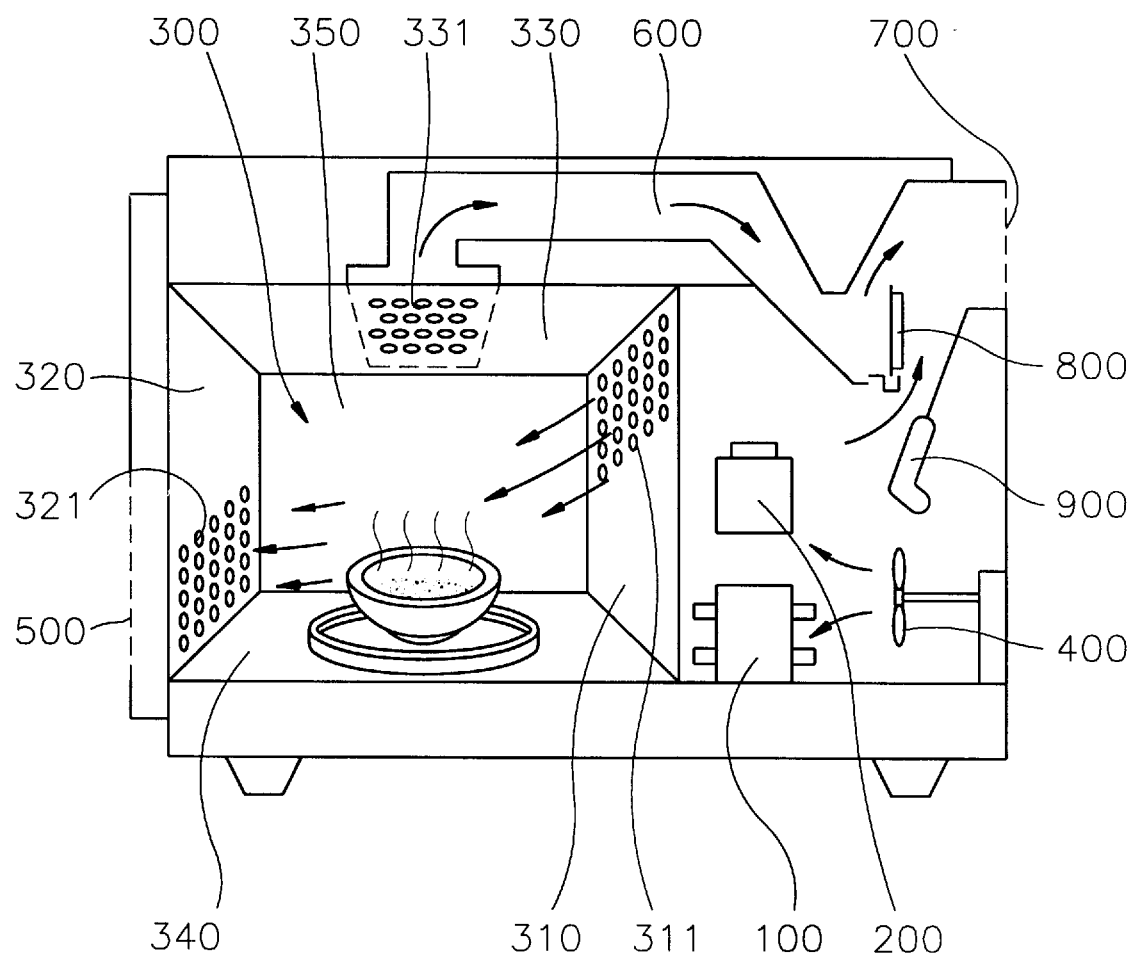
FIG. 1 is a schematic construction view for showing an internal structure of a general microwave oven equipped with a vapor sensor therein.

FIG. 1 is a schematic construction view for showing an internal structure of a general microwave oven equipped with a vapor sensor therein. As shown in FIG. 1, a microwave oven 10 includes a cavity 300 which is disposed at the left half portion thereof to form a cooking chamber, and is equipped with a variety of electric devices at the right half portion therein, which perform an automatic cooking operation of microwave oven 10. Cavity 300 includes a first sidewall 310 arranged on the right side, a second sidewall 320 arranged on the left side, a ceiling portion 330 arranged in the upper portion, a floor portion 340 arranged in the lower portion thereof, and a rear surface portion 350 arranged rearward. First sidewall 310 has first blow holes 311 in the upper portion thereof. Second sidewall 320 has first exhaust holes 321 in the lower portion thereof. Ceiling portion 330 has second exhaust holes 331 in a central portion thereof. A main body of microwave oven 10 includes first discharge holes 500 in the lower portion of the left outer wall. First discharge holes 500 are interconnected with first exhaust holes 321. The main body of microwave oven 10 has a wind path 600 arranged over cavity 300, and an inlet of wind path 600 is interconnected with second exhaust holes 331 included in ceiling portion 330 of cavity 300. The main body of microwave oven 10 further has second discharge holes 700 in the upper portion of the right outer wall thereof. Second discharge holes 700 are interconnected with an outlet of wind path 600.

Vapor sensor 800 is internally installed in the right half portion of the main body included in microwave oven 10, and detects water vapor generated from food subjected to heating while the automatic cooking operation is being performed. Also, the right half portion included in the main body of microwave oven 10 is internally equipped with a high voltage transformer 100 which applies high voltage electricity to a magnetron 200 which generates microwave, a fan motor 400 which promotes a blowing operation, and an orifice 900. A door (not shown) is installed in the front surface portion of cavity 300 and isolates cavity 300 from an external space during the automatic cooking operation.

Figure 2:
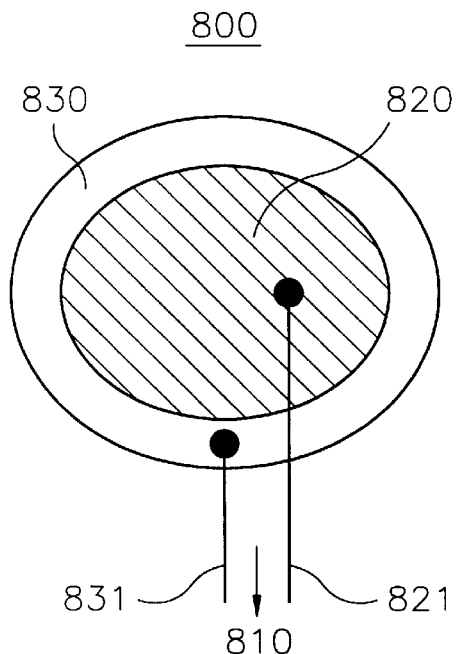
FIG. 2 is a construction view for showing an internal structure of a vapor sensor.
Figure 3:
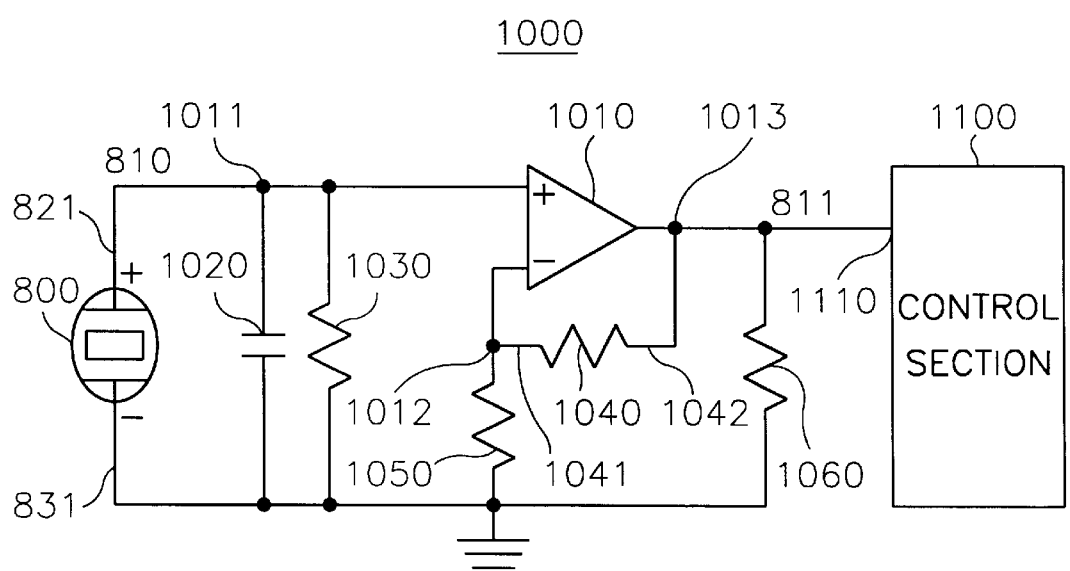
FIG. 3 is a circuit block diagram for showing a configuration of one embodiment of a detecting signal processing circuit section for processing a detecting signal supplied from the vapor sensor shown in FIG. 2.

FIG. 3 is a circuit block diagram for showing a configuration of one embodiment of a detecting signal processing circuit section for processing a detecting signal supplied from the vapor sensor shown in FIG. 2. In the detecting signal processing circuit section 1000 shown in FIG. 3, a first electrode terminal 821 corresponding to a positive electrode terminal of vapor sensor 800, is connected with a non-inverting(+) input terminal of an operational amplifier 1010 to form a first commonly-connecting point 1011, and a second electrode terminal 822 corresponding to the negative electrode terminal of vapor sensor 800, is connected with an earth connection. Condenser 1020 is connected between commonly-connecting point 1011 and the earth connection in order to refine the waveform of detecting signal 810. Also, a first resistor 1030 is connected between first connecting point 1011 and the earth connection in order to convert a current signal of detecting signal 810 supplied from vapor sensor 800 to a voltage signal. Operational amplifier 1010 amplifies detecting signal 810 generated from vapor sensor 800. A second resistor 1040 for a negative feedback is connected between the inverting(−) input terminal and the output terminal of operational amplifier 1010 in order to perform the negative feedback operation by feedbacking the portion of a current signal amplified by operational amplifier 1010. First side terminal 1041 of second resistor 1040 is connected with the inverting(−) input terminal of operational amplifier 1010 to form a second commonly-connecting point 1012. A third resistor 1050 is connected between second commonly-connecting point 1012 and the earth connection in order to apply a bias voltage to the inverting(−) input terminal of operational amplifier 1010. Second side terminal 1042 of second resistor 1040 is connected with the output terminal of operational amplifier 1010 to form a third commonly-connecting point 1013. A fourth resistor 1060 for the voltage output is connected between third commonly-connecting point 1013 and the earth connection in order to transform a current signal to a voltage signal. The output of operational amplifier 1010 is connected with a detecting signal input terminal 1110 of a control section 1100 in order to provide detecting signal 810 generated from vapor sensor 800 to control section 1100.

A measuring point of detecting signal 810 is first commonly-connecting point 1011 with which both the non-inverting(+) input terminal of operational amplifier 1010 and first electrode terminal 821 of vapor sensor 800 are directly connected. Detecting signal 810 at first commonly-connecting point 1011 has the waveform corresponding to the shape of an alternating current signal. However, the signal-processed detecting signal 811 outputted at third commonly-connecting point 1013 only has a positive value by the signal processing operation of operational amplifier 1010 which is an amplifying device.

In the present invention, first electrode terminal 821 connected with first disc 820 made of ceramic materials, is defined as a positive terminal (refer to FIG. 2). In this case, detecting signal 810 from vapor sensor 800 has the characteristics that detecting signal 810 at first commonly-connecting point 1011 increases in the positive voltage direction while vapor sensor 800 sucks in heat.

Figure 4:
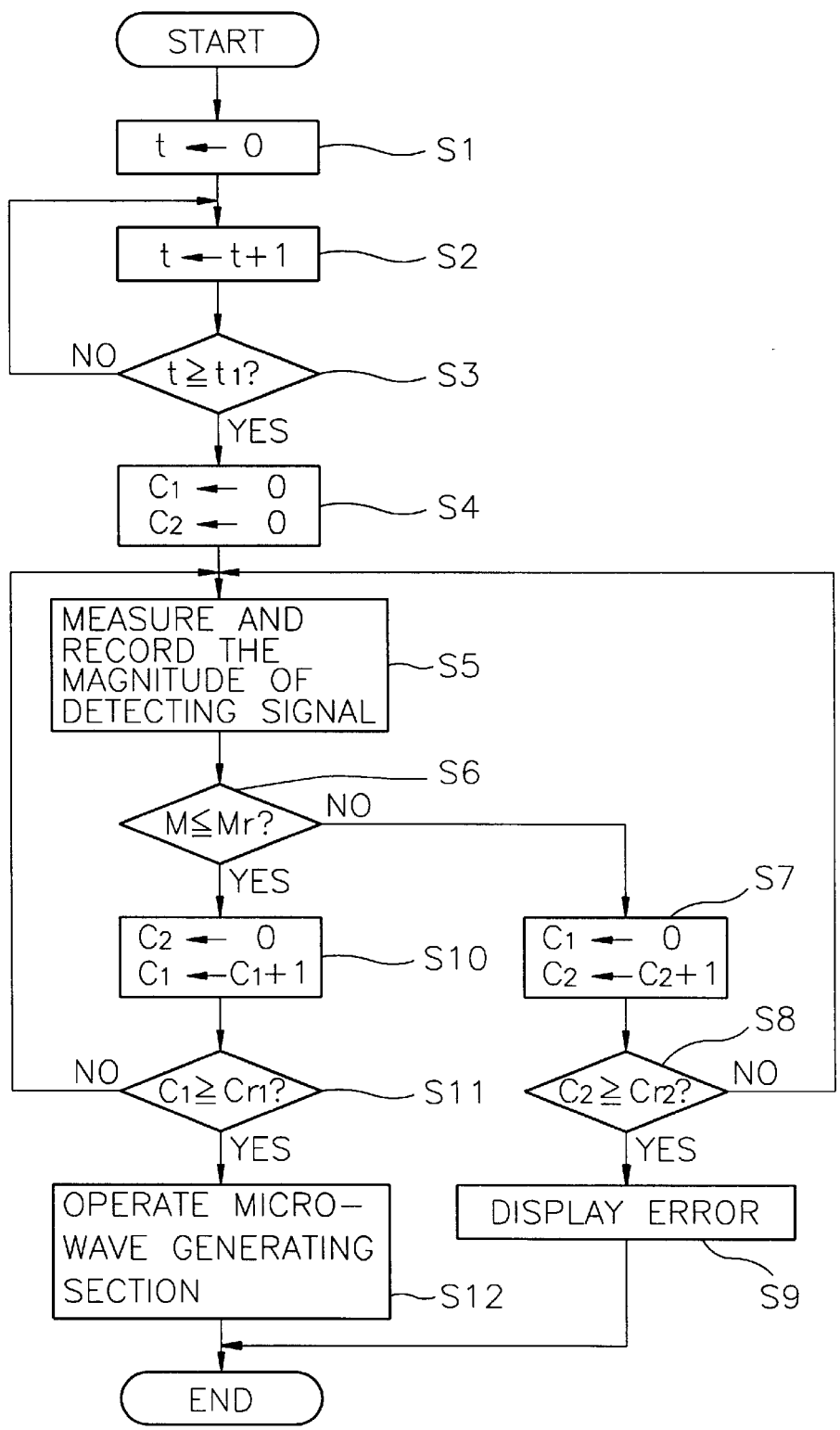
FIG. 4 is a flow chart for illustrating a polarity discriminating method for the vapor sensor in the microwave oven shown in FIG. 1.

FIG. 4 is a flow chart for illustrating a polarity discriminating method for the vapor sensor in the microwave oven shown in FIG. 1. FIG. 5 and FIG. 6 are respectively waveform diagrams for showing the waveforms of signal-processed detecting signals supplied from the detecting signal processing circuit section shown in FIG. 3. The waveforms of a signal-processed detecting signals 811 shown in FIG. 5 and FIG. 6, are the waveforms of the signals outputted at third commonly-connecting point 1013 of detecting signal processing circuit section 1000 shown in FIG. 3. As shown in FIG. 4, while the operation of automatically cooking food is executed by using microwave oven 10 having the above-described construction, control section 1100 (refer to FIG. 3) measures a magnitude M of signal-processed detecting signal 811 supplied from detecting signal processing circuit section 1000 which inputs and signal-processes detecting signal 810 supplied from vapor sensor 800, which is varied according to the temperature of air that sequentially passes through cavity 300 and wind path 600 to be discharged, and then discriminates the polarity of vapor sensor 800. Thereby, control section 1100 can perform a proper automatic cooking operation. As shown in FIG. 5 and FIG. 6, in the case where X-axis is a phase coordinate axis for indicating the value(C) of counter corresponding to a phase coordinate value, and Y-axis is a magnitude coordinate axis for indicating the value of a magnitude M, then in general, magnitude M of signal-processed detecting signal 811 supplied from detecting signal processing circuit section 1000 is greater than or smaller than the magnitude $M_r$ of the reference detecting signal corresponding to an objective value.

Namely, either a "positive polarity mode", when magnitude M of signal-processed detecting signal 811 is smaller than magnitude $M_r$ of the reference detecting signal, or a "negative polarity mode", when magnitude M of signal-processed detecting signal 811 is greater than the magnitude $M_r$ of the reference detecting signal, appears. Also, a slope sign of the curve in signal-processed detecting signal 811, has a positive polarity or a negative polarity in a specified range on the phase coordinate axis. Here, the slope means a differential value at a certain point indicated by a pertinent phase coordinate value and magnitude coordinate value. That is, the polarity of signal-processed detecting signal 811 is positive while vapor sensor 800 sucks in heat, but the polarity of signal-processed detecting signal 811 is negative while vapor sensor 800 discharges heat. Therefore, control section 1100 compares magnitude M of signal-processed detecting signal 811 with magnitude $M_r$ of the reference detecting signal in the specified range on the phase coordinate axis, and meanwhile, discriminates whether the slope of the curve in the range is positive or negative, so that control section 1100 can discriminates whether vapor sensor 800 operates in the positive polarity mode or the negative polarity mode.

In the meantime, it is difficult to discriminate the polarity of detecting signal 810 supplied from vapor sensor 800 because vapor sensor 800 repeats sucking in and discharging the heat in response to the temperature and the number of molecules of the water vapor generated from the food which is subjected to heating while the food is cooked automatically. However, the polarity of detecting signal 810 supplied from vapor sensor 800 is discriminated by means of the waveform of signal-processed detecting signal 811 because detecting signal 810 always has a predetermined waveform in response to the wind produced by means of fan motor 400 among environmental conditions to which vapor sensor 800 responses.

General electrical characteristics of detecting signal 810 supplied from vapor sensor 800 are affected not only by the environmental conditions such as the wind produced by fan motor 400, but also by the temperature of vapor sensor 800 and the amount of the water vapor which remains in cavity 300. Namely, various types of waveforms of detecting signal 810 are generated according to a variety of the environmental conditions. Magnitude M of signal-processed detecting signal 811 supplied from detecting signal processing circuit section 1000 is proportional to the temperature and the number of molecules in the water vapor generated from the food subjected to heating, and the above two factors also affect phase C of signal-processed detecting signal 811. Namely, magnitude M of signal-processed detecting signal 811 is affected by the temperature and the number of molecules in the water vapor, and the phase C of signal-processed detecting signal 811 is also affected by the number of molecules in the water vapor.

Therefore, it is assumed that no water vapor exists in cavity 300 in order to simplify the environmental conditions, so that during the automatic cooking operation a sufficient air cooling time is forcibly applied in order to discriminate whether a slope of the curve of signal-processed detecting signal 811 is positive or negative in a specified range on the phase coordinate axis by means of signal-processed detecting signal 811 which is generated from vapor sensor 800 in response to the wind produced by fan motor 400 and then signal-processed by detecting signal processing circuit section 1000.

As shown in FIG. 4, if a user adjusts a start key (not shown) to the 'ON' state in order to initiate the automatic cooking operation, control section 1100 recognizes the 'ON' state of the start key and applies a control signal to a load driving section (not shown). At this time, control section 1100 initializes to zero operating time t of fan motor 400 in step S1 and increases present operating time t of fan motor 400 by "1" in step S2. The load driving section operates a blowing section such as fan motor 400 for the operating time increased by "1" in order to start the blowing operation which blows cavity 300 through first blow holes 311 formed in the upper portion of first sidewall 310 (step S2). In step S3, control section 1100 judges whether or not the operating time t of fan motor 400, which is increased by "1" in step S2, is greater than or equal to predetermined time $t_1$.

If operating time t is smaller than predetermined time $t_1$, control section 1100 returns to step S2 and repeatedly performs the blowing operation of fan motor 400. Thereby, control section 1100 air-cools cavity 300 and removes the water vapor which remains in cavity 300. If operating time t is greater than or equal to predetermined time $t_1$, control section 1100 initializes to zero both first and second variables $C_1$ and $C_2$ of the first and the second counters (not shown) in order to measure the output of vapor sensor 800 in step S4.

In the meantime, the wind, i.e., the flow of air produced by fan motor 400, flows out from first blow holes 311 formed in the upper portion of first sidewall 310 of cavity 300 and passes sequentially through first exhaust holes 321 formed in the lower portion of second sidewall 320 disposed in opposition to first sidewall 310 and through first discharge holes 500, and is then discharged. Also, the wind passes sequentially through second exhaust holes 331 formed in the central portion of ceiling portion 330 of cavity 300, through wind path 500 and through second discharge holes 700, and is then discharged. At this time, because the wind discharged through wind path 500 is sensed by vapor sensor 800 installed at the inlet of second discharge holes 700, control section 1100 measures magnitude M of signal-processed detecting signal 811 supplied from detecting signal processing circuit section 1000 in step S5, and stores magnitude M of signal-processed detecting signal 811 in a memory device (not shown). Control section 1100 judges whether or not magnitude M of signal-processed detecting signal 811 is equal to or smaller than magnitude $M_r$ of the reference detecting signal.

FIG. 5 and FIG. 6 are respectively waveform diagrams for showing the waveforms of signal-processed detecting signals supplied from the detecting signal processing circuit section shown in FIG. 3. As shown in FIG. 6, if magnitude M of signal-processed detecting signal 811 is greater than magnitude $M_r$ of the reference detecting signal in a specified range on the phase coordinate axis, control section 1100 sets both first and second variables $C_1$ and $C_2$ of the first and the second counters respectively in step S7, according to the following equation 1.

$$C_1 \leftarrow 0$$
$$C_2 \leftarrow C_2 + 1 \qquad\qquad \text{equation 1}$$

In step S8, control section 1100 judges whether or not second variable $C_2$ of the second counter, which is increased by "1" in step S7, is greater than or equal to second variable $C_{r2}$ of the reference detecting signal. If second variable $C_2$ of the second counter is smaller than second variable $C_{r2}$ of the reference detecting signal, control section 1100 returns to step S5 and repeatedly performs the succeeding steps. If second variable $C_2$ of the second counter is greater than or equal to second variable $C_{r2}$ of the reference detecting signal, an erroneous state is displayed on a control and display panel disposed on the front surface portion of microwave oven 10, and then a general cooking operation which is in process is stopped.

If present magnitude M of signal-processed detecting signal 811, as shown in FIG. 5, is equal to or smaller than magnitude $M_r$ of the reference detecting signal in a specified range on the phase coordinate axis, control section 1100 sets both first and second variables $C_1$ and $C_2$ of the first and the second counters respectively in step S10, according to the following equation 2.

$$C_2 \leftarrow 0$$
$$C_1 \leftarrow C_1 + 1 \qquad \text{equation 2}$$

In step S11, control section 1100 judges whether or not first variable $C_1$ of the first counter, which was increased by "1" in step 10, is greater than or equal to first variable $C_{r1}$ of the reference detecting signal. If first variable $C_1$ of the first counter is smaller than first variable $C_{r1}$ of the reference detecting signal, control section 1100 returns to step S5 and repeatedly performs the succeeding steps. If first variable $C_1$ of the first counter is greater than or equal to first variable $C_{r1}$ of the reference detecting signal, control section 1100 operates a microwave generating section such as magnetron 200 and performs a heating operation, i.e., one example of the automatic cooking operation.

Thereby, by means of the blowing operation of fan motor 400, the microwave energy supplied from magnetron 200 is delivered into the inner part of the cooking chamber through first blow holes 311 formed at the upper portion of first sidewall 310 included in cavity 300, and radiates to heat the food.

In the polarity discriminating method and signal processing circuit for a vapor sensor in a microwave oven according to the present invention, the polarity, varied in accordance to wind produced by fan motor 400, of detecting signal 810 supplied from vapor sensor 800, is automatically discriminated, so that the malfunction of a driving circuit of microwave oven 10 can be prevented. Also, in the detecting signal processing circuit section for the vapor sensor in the microwave oven, the configuration of the circuit is simplified to cut down the cost required for manufacturing the circuit and to reduce the volume of the circuit.

Therefore, the performance and the life span of the microwave oven are significantly enhanced to heighten the user's sense of reliability concerning the performance of the microwave oven and to fulfill the consumer's intention with which the microwave oven is purchased.

While the present invention has been particularly shown and described with reference to a particular embodiment thereof, it will be understood by those skilled in the art that various changes in form and detail may be effected therein without departing from the spirit and scope of the invention which is defined by the appended claims.

What is claimed is:

1. A method for discriminating the polarity of a vapor sensor in a microwave oven, said method comprising the steps of:
   (i) operating a blowing means for an operating time by a control means so as to remove water vapor which remains in a cavity of the microwave oven, thereby air-cooling the cavity while food is being cooked by using the microwave oven equipped with the vapor sensor therein;
   (ii) initializing to zero both a first variable of a first counter and a second variable of a second counter in order to measure a magnitude of a signal-processed detecting signal supplied from a detecting signal processing circuit which inputs and signal-processes a detecting signal supplied from the vapor sensor;
   (iii) recording a measured magnitude of the signal-processed detecting signal supplied from the detecting signal processing circuit in response to a wind which is produced by the operation of the blowing means and which passes sequentially through second exhaust holes formed in a central portion of a ceiling portion of the cavity, through a wind path and through second discharge holes;
   (iv) initializing to zero either the first variable of the first counter or the second variable of the second counter, and increasing either the first variable of the first counter or the second variable of the second counter by a first predetermined amount in accordance with the measured magnitude of the signal-processed detecting signal; and
   (v) either indicating an error state or operating a microwave generating means in accordance with either a value of the first variable of the first counter or a value of the second variable of the second counter.

2. The method for discriminating the polarity of a vapor sensor in a microwave oven as claimed in claim 1, wherein said step (i) comprises the substeps of:
   (a) initializing to zero the operating time of the blowing means;
   (b) increasing the operating time of the blowing means by a second predetermined amount;
   (c) judging whether or not the operating time of the blowing means increased by the second predetermined amount in step (b) is greater than or equal to a predetermined time;
   (d) returning to step (b) and repeating the succeeding steps when it is judged in step (c) that the operating time of the blowing means is smaller than the predetermined time; and
   (e) performing step (ii) when it is judged in step (c) that the operating time of the blowing means is greater than or equal to the predetermined time.

3. The method for discriminating the polarity of a vapor sensor in a microwave oven as claimed in claim 1, wherein said step (iv) comprises the substeps of:
   (f) judging whether or not the measured magnitude of the signal-processed detecting signal is smaller than or equal to a magnitude of a reference detecting signal;
   (g) initializing to zero the first variable of the first counter and increasing the second variable of the second counter by the first predetermined amount when it is judged in step (f) that the magnitude of the signal-processed detecting signal is greater than the magnitude of the reference detecting signal; and
   (h) increasing the first variable of the first counter by the first predetermined amount and initializing to zero the second variable of the second counter when it is judged in step (f) that the magnitude of the signal-processed detecting signal is smaller than or equal to the magnitude of the reference detecting signal.

4. The method for discriminating the polarity of a vapor sensor in a microwave oven as claimed in claim 1, wherein said step (v) comprises the substeps of:
   (k) judging whether or not the second variable of the second counter increased by the first predetermined amount in step (iv) is greater than or equal to a second variable of a reference detecting signal;
   (l) returning to step (iii) and repeating the succeeding steps when it is judged in step (k) that the second variable of the second counter is smaller than the second variable of the reference detecting signal;
   (m) indicating an error state when it is judged in step (k) that the second variable of the second counter is greater than or equal to the second variable of the reference detecting signal;
   (n) judging whether or not the first variable of the first counter increased by the first predetermined amount in step (iv) is greater than or equal to a first variable of the reference detecting signal;

(o) returning to step (iii) and repeating the succeeding steps when it is judged in step (n) that the first variable of the first counter is smaller than the first variable of the reference detecting signal; and (p) operating the microwave generating means by a load driving means when it is judged in step (n) that the first variable of the first counter is greater than or equal to the first variable of the reference detecting signal.

5. A method for discriminating the polarity of a vapor sensor in a microwave oven, said method comprising the steps of:

(a) initializing to zero an operating time of a blowing means;

(b) increasing the operating time of the blowing means by a first predetermined amount;

(c) judging whether or not the operating time of the blowing means increased by the first predetermined amount in step (b) is greater than or equal to a predetermined time;

(d) returning to step (b) and repeating the succeeding steps, when it is judged in step (c) that the operating time of the blowing means is smaller than the predetermined time;

(e) initializing to zero both a first variable of a first counter and a second variable of a second counter in order to measure a magnitude of a signal-processed detecting signal supplied from a detecting signal processing circuit which inputs and signal-processes a detecting signal supplied from the vapor sensor, when it is judged in step (c) that the operating time of the blowing means is greater than or equal to the predetermined time;

(f) recording a measured magnitude of the signal-processed detecting signal supplied from the detecting signal processing circuit in response to a wind which is produced by the operation of the blowing means and which passes sequentially through second exhaust holes formed in a central portion of a ceiling portion of a cavity of the microwave oven, through a wind path and through second discharge holes;

(g) judging whether or not the measured magnitude of the signal-processed detecting signal is smaller than or equal to a magnitude of a reference detecting signal;

(h) initializing to zero the first variable of the first counter and increasing the second variable of the second counter by a second predetermined amount when it is judged in step (g) that the magnitude of the signal-processed detecting signal is greater than the magnitude of the reference detecting signal;

(i) increasing the first variable of the first counter by the second predetermined amount and initializing to zero the second variable of the second counter when it is judged in step (g) that the magnitude of the signal-processed detecting signal is smaller than or equal to the magnitude of the reference detecting signal;

(j) judging whether or not the second variable of the second counter increased by the second predetermined amount in step (h) is greater than or equal to a second variable of the reference detecting signal;

(k) returning to step (f) and repeating the succeeding steps when it is judged in step (j) that the second variable of the second counter is smaller than the second variable of the reference detecting signal;

(l) indicating an error state when it is judged in step (j) that the second variable of the second counter is greater than or equal to the second variable of the reference detecting signal;

(m) judging whether or not the first variable of the first counter increased by the second predetermined amount in step (i) is greater than or equal to a first variable of the reference detecting signal;

(n) returning to step (F) and repeating the succeeding steps when it is judged in step (M) that the first variable of the first counter is smaller than the first variable of the reference detecting signal; and (o) operating a microwave generating means by a load driving means when it is judged in step (M) that the first variable of the first counter is greater than or equal to the first variable of the reference detecting signal.

* * * * *